(12) United States Patent
Genosar

(10) Patent No.: US 11,185,634 B2
(45) Date of Patent: Nov. 30, 2021

(54) BENEFICIAL AGENT DISPENSER

(71) Applicant: AktiVax, Inc., Broomfield, CO (US)

(72) Inventor: Amir Genosar, Aurora, CO (US)

(73) Assignee: AKTIVAX, Inc., Broomfield, CO (US)

(*) Notice: Subject to any disclaimer, the term of this patent is extended or adjusted under 35 U.S.C. 154(b) by 220 days.

(21) Appl. No.: 15/792,330

(22) Filed: Oct. 24, 2017

(65) Prior Publication Data
US 2018/0243505 A1    Aug. 30, 2018

Related U.S. Application Data

(63) Continuation of application No. 13/884,246, filed as application No. PCT/US2011/059807 on Nov. 8, 2011, now abandoned.

(60) Provisional application No. 61/432,217, filed on Jan. 13, 2011, provisional application No. 61/410,940, filed on Nov. 8, 2010.

(51) Int. Cl.
A61M 5/24     (2006.01)
A61M 5/19     (2006.01)
A61M 5/28     (2006.01)
A61M 5/315    (2006.01)
A61M 5/50     (2006.01)
A61J 1/20     (2006.01)
A61J 1/06     (2006.01)

(52) U.S. Cl.
CPC ............ *A61M 5/2448* (2013.01); *A61J 1/067* (2013.01); *A61J 1/2093* (2013.01); *A61J 1/2096* (2013.01); *A61M 5/19* (2013.01); *A61M 5/2425* (2013.01); *A61M 5/2455* (2013.01); *A61M 5/282* (2013.01); *A61M 5/284* (2013.01); *A61M 5/285* (2013.01); *A61M 5/315* (2013.01); *A61M 5/50* (2013.01)

(58) Field of Classification Search
CPC ...... A61M 5/2448; A61M 5/50; A61M 5/315; A61M 5/285; A61M 5/284; A61M 5/282; A61M 5/2455; A61M 5/2425; A61M 5/19; A61M 5/2451; A61M 5/245; A61J 1/2096; A61J 1/2093; A61J 1/067
See application file for complete search history.

(56) References Cited

U.S. PATENT DOCUMENTS

2001/0047162 A1* 11/2001 Yugari .................. A61M 5/282
                                                        604/410

* cited by examiner

Primary Examiner — Lauren P Farrar
Assistant Examiner — Hamza A Darb
(74) Attorney, Agent, or Firm — Holzer Patel Drennan

(57) ABSTRACT

A dispensing device for use with a beneficial agent has a dispensing package, a dispenser disposed on an end portion of the dispensing package, and an actuator movably disposed along at least a portion of the package between a pre-dispensing state and a dispensing state. One arrangement also provides a beneficial agent dispenser having a dispensing port, an elongate portion and a plunger that is movably disposed relative to a tubular wall of the elongate portion during a dispensing stroke to partially penetrate a separable barrier and expel the beneficial agent through the dispensing port.

9 Claims, 9 Drawing Sheets

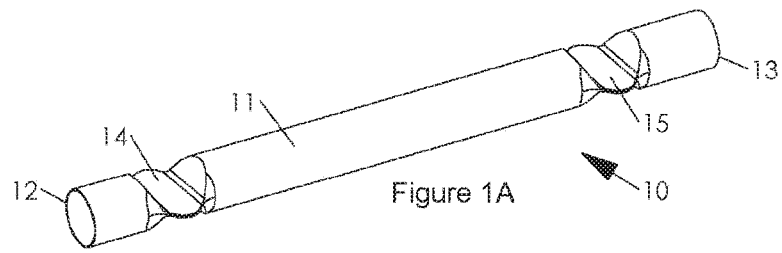
Figure 1A
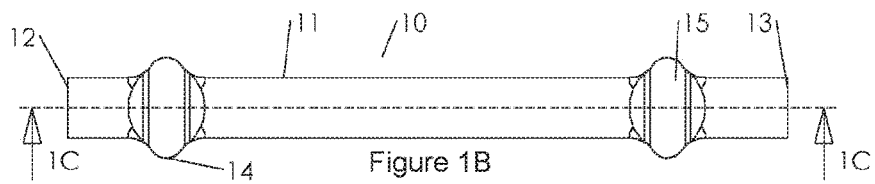
Figure 1B
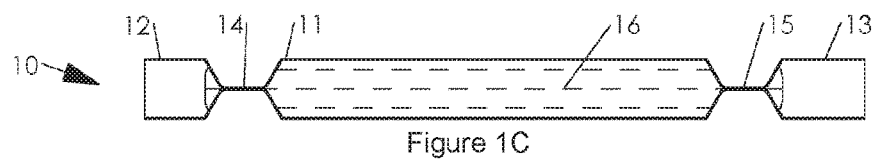
Figure 1C
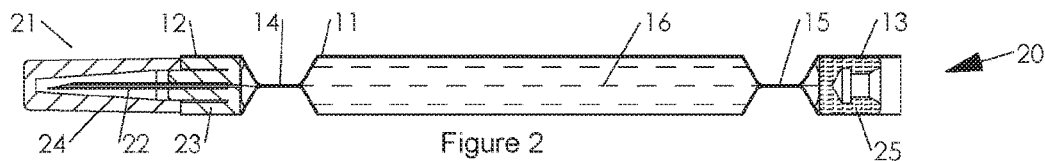
Figure 2
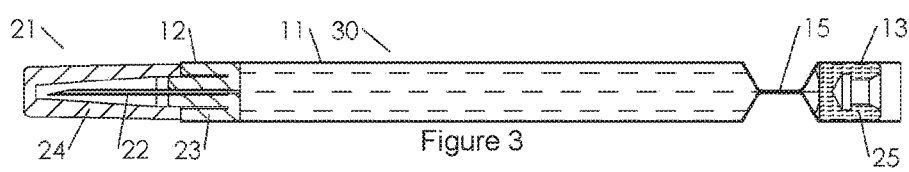
Figure 3
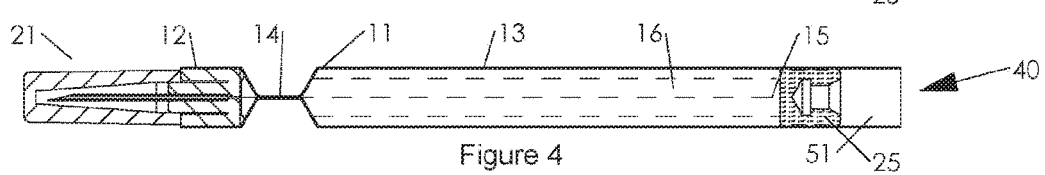
Figure 4
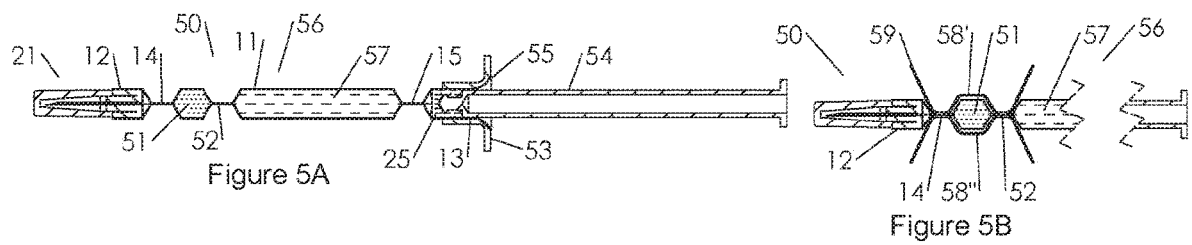
Figure 5A
Figure 5B

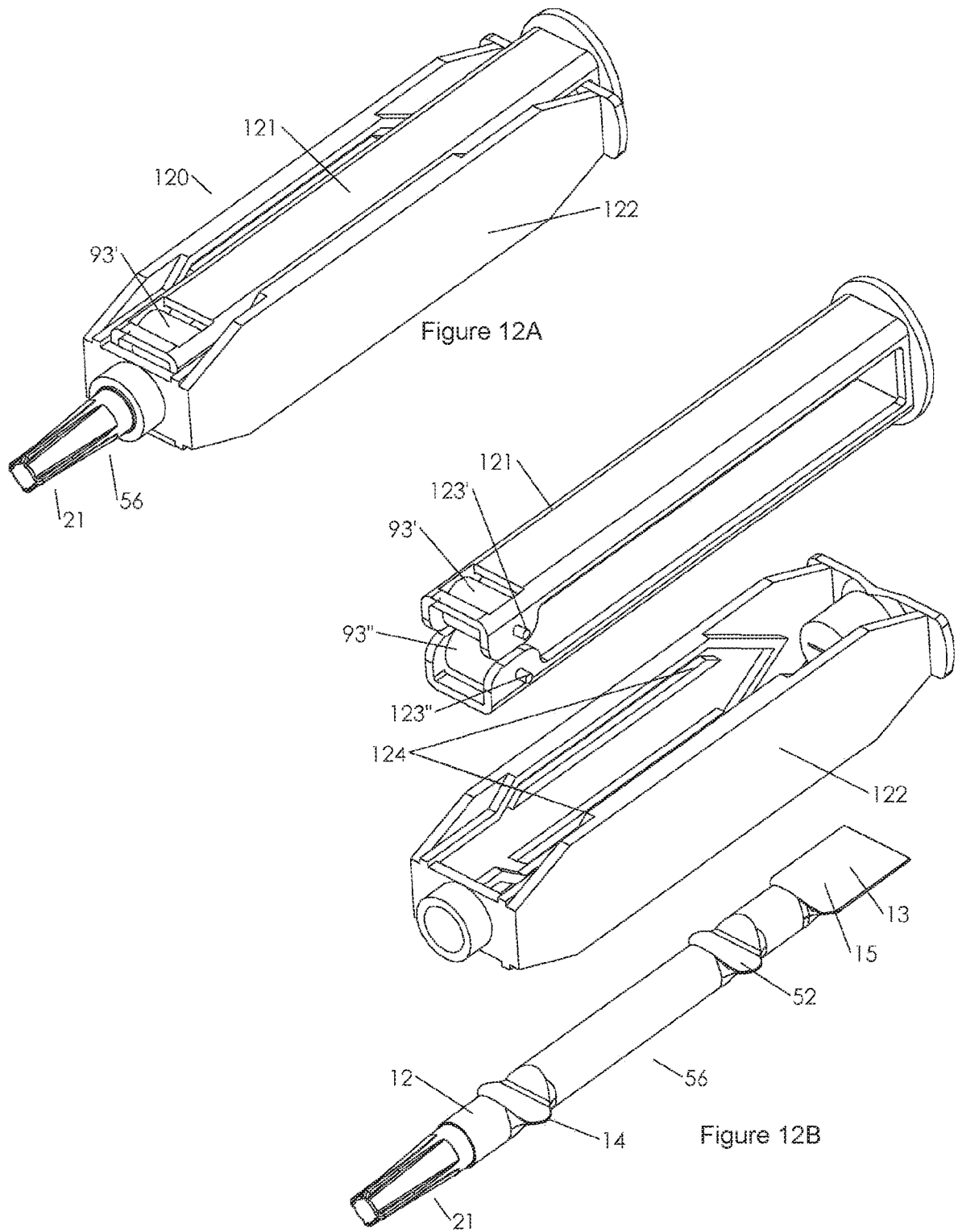

BENEFICIAL AGENT DISPENSER

FIELD

The present disclosure preferably, but without limitation, generally pertains to prefilled single use, single dose dispensing devices. More specifically, the present disclosure pertains to dispensing packages for administration of beneficial agents, namely, medication.

DESCRIPTION OF THE BACKGROUND

Several commercial single dose dispensing packages are in a fashion of a syringe where a piston comprising a plunger, comprising a sealing surface, is introduced at a proximal end of a barrel comprising a dispensing port at its distal end; said piston is disposed in a movable fashion along the axis of said plunger and barrel. The plunger seals against the internal wall of the barrel to form a chamber for a dispensable product, and the arrangement is such that the piston and plunger are movable toward said dispensing port of the barrel to deplete the volume of said product chamber thereby forcing the product to dispense through the dispensing port. Such syringe barrels are typically made from clear plastic or glass and the plunger is typically made from chemically stable rubbers.

In drug delivery applications, the most common practice with syringe products is that the syringe is filled at the time of use (typically by a caregiver). In some drug delivery applications, it is desired that the syringe will be prefilled and serve as a primary container for the dispensable product for a defined duration and at specific conditions; in which case, it is required to limit the interactions between the primary package materials and the product that may affect the product composition or properties. It is also desired to limit the dispensable product, or elements of it, from migrating out of the package, or materials migrating to the dispensable product from the package's walls or through the package's wall (i.e. the plunger, barrel, etc.) These product stability requirements present a challenge in some industries including the pharmaceutical industry. Molded plastic syringe barrels suffer from relatively high moisture and oxygen transferability, specifically Polypropylene (PP) and Polyethylene (PE). In recent years, new commercial moldable plastic materials provide higher moisture and gas barriers such as Cyclic Olefin Copolymer (COC) and Cyclo Olefin Polymer (COP), yet their barrier properties are limited compared to glass or high barrier films which are typically used in the pharmaceutical industry as a primary package for elongated shelf life. Glass syringe barrels, on the other hand, present other challenges as a primary container. For one, it is becoming more obvious in recent years that residues of tungsten in the barrel resulting from wear of the tools used for forming the glass present a problem for stability of certain products. In addition, the friction between the rubber plunger and the glass barrel during dispensing is high and is commonly addressed in the industry by coating the inner side of the barrel with lubricants (typically silicone lubricants) which also affect certain products' stability and, in particular, has been shown to cause protein aggregation which affect the potency of some protein based drugs. The lubricants do not completely solve the slip force problem with glass syringes which remains an undesirable property of glass syringes. In some pharmaceutical applications, and particularly for stability and shelf life purposes, it is desired to store a dispensable product as separate substances that are mixed at a time of use to form the dispensable product just prior to dispensing. As one example, certain drug or vaccines are preserved in dry format to extend their shelf life and reduce their thermal sensitivity, and are mixed with a diluent just prior to injection to a patient. Some prefilled syringes have been developed to address these applications and provide a primary container having two storage compartments for two substances (commonly, one is for the dry drug or vaccine, and the other is for the diluent). These syringes are constructed such that the two substances are mixed by a certain manipulation of the syringe prior to the injection step, the last being very similar to the injection procedure with a regular syringe. These syringes are typically made from glass or COC/COP and commercial products are commercially available from Vetter (Ravensburg, Germany).

U.S. Pat. No. 6,817,987 teaches a mixing hypodermic syringe holding a solvent and a soluble component that has a tubular body formed at its front and rear ends with a bypass, a plunger axially slidable in the body, and a stem projecting axially rearward out of the body from the plunger. A cover fits over the front end of the body and is so tight that the front compartment can be pressurized to a super atmospheric pressure without leakage out the front end. A free piston slidable in the body forward of the plunger subdivides the body forward of the plunger into a front compartment at the front body end holding the soluble component and a rear compartment between the plunger and the piston holding the solvent. Stops are provided for arresting the free piston when it is level with the bypass in a position permitting flow through the bypass between the compartments. However, there are several drawbacks with this approach: (a) the barrel is made from glass or molded plastic which presents the problems discussed above, (b) the additional piston complicates the product and adds to its bill of material cost and manufacturing costs, (c) the extra piston limits the ability to mix between the two compartments to form a uniform dispensable product, and (d) it does not provide needle-stick safety and post-use disabling features which are becoming a more regular requirement in the medical field.

SUMMARY

The present disclosure overcomes the disadvantages and limitations of the prior art by providing a low cost, simple and easy to use dispensing device, preferably formed as a package, that allows the user to dispense the contents of the package in a controlled manner through a fluid transport device, also referred to as a dispenser. As used herein, the term "fluid transport device" generally refers to any means for transporting a flowable product having at least one inlet port for introducing the product and at least one outlet port to dispense the product. Examples of fluid transport devices include a spout, a connector, a fitting, a Luer Slip connector/fitting, a Luer Lock connector, a needle, a hypodermic needle, a mini-needle, a set of mini needles, a micro needle, an array of micro needles, a tube or a pipe, a spray head, an oral dropper, a nasal dropper or sprayer, an eye dropper or sprayer, a topical applicator, a jet injector an adaptor to any of the above, an adapter to an absorbent material (such as a sponge, woven or none-woven pads, or a cloth that may be used to apply a substance to a surface such as the skin). The fluid transport device may further comprise a cap, a valve, a septum, a stopper or a tap for sealing the outlet port, which may be used to allow multi-dose dispensing from the package. A one way valve (check valve) may be formed in the fluid transport device, to avoid refill and reuse of the device.

According to the present disclosure there is now a dispensing device substantially resembling the form of a hypodermic syringe, comprising an elongate member (referred to at times as a "barrel") comprising a tubular wall partially defining at least one compartment of a dispensable product (or "product"). The barrel comprises a proximal end and a distal end; said distal end is associated with a fluid transport device. The product compartment can be manipulated to reduce its volume forcing the product to advance in the barrel. At least one portion of the tubular wall of the barrel comprises a thin collapsible wall, substantially thinner than the wall of a typical hypodermic syringe. The thin wall is pinched in certain areas to form a separable barrier defining a wall of said compartment. The tubular wall may be made from high barrier material. In one arrangement the tubular wall is made from multi-layer plastic material. The high barrier layer can be made from polychlorotrifluoroethylene (PCTFE) commercially branded by Honeywell as Aclar or COC. In one arrangement the inner layer of the tubular wall material is made from an adhesive material such that it can be deformed (pinched) and sealed to itself or to a second component to form a barrier. In one arrangement said adhesive material is a thermal adhesive which bonds the pinched section of the tubular wall under the presence of a threshold temperature. A number of olefin polymers can provide for the thermally adhesive inner layer of the tubular wall including olefin ionomer blend such as the commercial brand EasyPeel™ from Bemis (Oshkosh, Wis.). The tubular wall can be made by various methods known in the art including extrusion, co-extrusion, molding, or rolling of a film material. The inner adhesive layer of the tubular wall can be made by any of the methods known in the art including co-extrusion with other layers of the tubular wall, coating, blown from a thin sleeve inside the tubular wall, etc. The adhesive layer can be applied throughout the inner side of the tubular wall or applied to selective sections on the inner side of the tubular wall. A lubricant component can be blended in the inner layer to improve the slip of a plunger in the barrel. In one arrangement, the tubular wall is produced by a process which includes the following steps: (a) a high barrier film is unwound from a roll, (b) the leading end of said high barrier film is rolled around an extrusion head such that its longitudinal fringes align or slightly overlap, (c) the longitudinal rolled film is fed to a calendar and the extrusion head extrudes an internal cylindrical layer bonded to the high barrier rolled film, forming a tube, (d) the tube is cooled and then cut into sections. In some arrangements, the high barrier film is printed or otherwise marked with visual information. In some arrangements, an external tubular layer is extruded onto the rolled sheet such that the high barrier film is confined between an inner tubular extruded layer and an outer extruded layer. In another arrangement, the tubular wall comprises a high barrier layer made from a rolled film or foil, and an inner layer extruded onto and bonded to the rolled layer, and the bonding is such that at least a section of the rolled layer is peelable from the extruded layer. In another arrangement, the tubular wall is produced by inserting a portion of a high barrier film or foil into the female side of a plastic injection mold such that its longitudinal fringes are aligned or slightly overlapping; molding an inner tubular layer bonded to the tubular high barrier section, in a similar fashion to an in-mold-labeling process, which is well know in the art of injection molding. The molded portion of the tubular section may further include details, such as finger flange and a tip. The rolled high barrier section may be printed or otherwise marked with visual information. Similar process may be implemented with blow molding or blow-fill-seal process where the molded material is blown onto the inner side of a high barrier film or foil rolled portion that is inserted into the mold.

The barrier, or barriers, at the pinched sections along the tubular wall are made such that they burst upon the presence of a threshold pressure in the compartment. In one arrangement, a pinched section of the tubular wall forms a barrier between the product compartment and the fluid transport device at the distal end of the barrel. In one arrangement, a pinched section of the tubular wall forms a barrier between the product compartment and the proximal end of the barrel. In one arrangement, a pinched section of the tubular wall forms a barrier between a first substance compartment and a second substance compartment along the barrel. When the barrier is ruptured, the first substance and the second substance are allowed to mix to form the dispensable product. In some arrangements, more than two compartments are formed along the barrel holding different substances which form the dispensable product when mixed. The threshold pressure needed to rupture the barriers along the barrel can be similar or different. There are various actuators which can be used to accomplish this. In one arrangement, the volume of the compartment, or compartments, is reduced by advancing a plunger in an axial direction along the compartment. In one arrangement, the volume of the compartment, or compartments, is reduced by compressing the tubular wall. In one arrangement, the tubular wall is compressed by a compression panel. In another arrangement, the tubular wall is compressed by a roller. The volume reduction of the compartment causes at least one of: (a) rupturing a barrier between the proximal end of the barrel and the first compartment, (b) rupturing a barrier between a first compartment and a second compartment, (c) rupturing a barrier between a compartment and the fluid transport device, and (d) dispensing the fluid out of the barrel through the fluid transport device. The dispensable product is dispensed by manipulating the device to reduce the compartment volume after the barrier between the compartment and the fluid transport device is ruptured. In some arrangements, a stem is provided to facilitate the axial manipulation which causes the volume reduction of the compartment. Finger flanges may be associated with the proximal end of the barrel. Said finger flanges may be made from molded plastic and attached to the barrel through one of the means known in the art including adhesives, one of the methods of heat welding, or through a mechanical lock. In one arrangement, the proximal end of the tubular wall is flared to provide a substantially radial surface for engagement with the finger flanges. The fluid transport device may have a molded plastic interface to engage with distal end of the barrel. This engagement may be accomplished by one of the methods known in the art including adhesion, heat welding, or mechanical engagement, such as a tight co-annular fit between the tubular wall and a cylindrical interface of the fluid transport device.

In some arrangements, the barrel is further supported by a rigid sheath, substantially extending along the barrel's axis between the proximal and the distal end of the barrel. In one arrangement, the sheath supports the fluid transport device. In one arrangement, the sheath provides the finger flanges. The sheath is engaged with the barrel by one of the methods known in the art including mechanical fit, adhesion, or heat welding. In one arrangement, the device is a hypodermic syringe comprising a needle-stick safety feature. In one arrangement, the needle is biased by a spring toward the proximal end of the barrel and is arrested in its position by a detent feature until the plunger reaches the distal end of the barrel, at which point, the needle is released to retract into the barrel such that its sharp point is protected and cannot be reached by a person at the normal course of use of the device. In another arrangement, the needle assembly clings to the plunger when the last reaches the proximal end of the barrel, such that when the plunger is retracted, the needle is withdrawn into the barrel to a protected position. This action also disables the syringe from subsequent use. Other needle safety features and subsequent use disabling features are applicable to the device of the present disclosure. In some arrangements, one compartment contains a soluble substance and a second compartment contains a diluent. An aseptic cap may be disposed to seal over the fluid transport device to maintain its sterility and/or a moisture and oxygen barrier until use. In some arrangements, the product is packaged in an aseptic package to maintain its sterility. In one arrangement, the device package further contains a drying agent, such as a desiccant material, to further limit the moisture that could penetrate the soluble substance's compartment.

One preferred method for filling a dual compartment reconstitution syringe of the present disclosure, with 0.5 ml of diluent and 0.2 ml of active powder, is described below:

Step 1: The tubular wall is extruded as a multilayer tube comprising an inner layer made from EasyPeel™, a middle layer made from Aclar™, and an outer layer made from PET, together forming a wall 150 microns thick; typically for this dose volume, an inner diameter of 3.5 mm to 4.5 mm is preferable;

Step 2: The extruded tube is cut to the desired tubular wall length; typically for this dose volume, a length of 50 mm to 65 mm is preferable;

Step 3: The tubular wall is pinched and heat welded along approximately 3 mm at the crimp location, dividing the tubular wall into two sections each opened to an opposite end of the tubular wall. Typically, a 140° C. temperature is desired with EasyPeel adhesive to form a good seal yet with weak peeling force;

Step 4: Vertically filling an aliquot powder dose through the distal end of the tubular wall by one of the powder filling methods known in this industry, such as the Höfliger Harro Verpackungsmaschinen GmbH (Allmersbach i.T.) Drum Filler;

Step 5: Crimping and sealing between the distal end of the tubular wall and the powder dose to form a sealed compartment of the powder;

Step 6: Vertically filling an aliquot of diluent dose through the proximal open end of the tubular wall with a metering dose pump;

Step 7: Crimping and heat sealing between the proximal end of the tubular wall and the diluent dose to form a sealed diluent compartment;

Step 8: Introducing a needle assembly, including a stainless steel needle, a cylindrical molded plastic needle hub, and a needle-protecting cap, by inserting the proximal end of the needle hub in a tight fit fashion into the distal end of the tubular wall;

Step 9: Introducing a plunger into the proximal end of the tubular wall;

Step 10: Heat welding the tubular wall to the needle-hub;

Step 11: Flaring the proximal end of the tubular wall;

Step 12: Axially introducing the sheath over the tubular wall;

Step 13: Heat welding the flare of the tubular wall to a reciprocal surface at the proximal end of the sheath;

Step 14: Engaging a stem with the plunger; and

Step 15: Seaing in a sterile pouch.

Some of the steps of this process may be performed in an aseptic environment with the components pre-sterilized to avoid terminal sterilization. In other cases, the aseptic environment may be avoided if the device can withstand terminal sterilization. In some arrangements, Step 5 may be avoided and the powder compartment merely sealed by the needle assembly (as in Step 8). In some arrangements, Step 7 may be avoided and the diluent compartment merely sealed by the plunger (as in Step 9). In some arrangements, Steps 1-7 are implemented, then Step 15, to create a sterile cartridge to be introduced to a delivery device at a later stage. In one arrangement, this later stage is accomplished on a different manufacturing line. In another arrangement, this later stage is accomplished by the user. In some arrangements, Steps 1-8 are implemented, then Step 15, to create a sterile cartridge to be introduced to a delivery device at a later stage. In one arrangement, this later stage is accomplished on a different manufacturing line. In another arrangement, this later stage is accomplished by the user. In some arrangements, Steps 1-9 are implemented, then Step 15, to create a sterile cartridge to be introduced to a delivery device at a later stage. In one arrangement, this later stage is accomplished on a different manufacturing line. In another arrangement, this later stage is accomplished by the user. In some arrangements, Steps 1-13 are implemented, then Step 15, where the stem is packed in the sterile pouch alongside the barrel assembly to reduce the overall shipping volume. The stem may be introduced to the plunger by the user.

In another preferred manufacturing method, at least one of the first substance, the second substance, the fluid transport device, or the plunger is introduced to the tubular wall on the tubular wall's extrusion line. Several patents and commercial products, such as the ones taught by U.S. Pat. Nos. 5,111,996 and 4,824,025, employ a method for introducing a desired component into an extruded tube during the tube extrusion. General examples of this method are taught by U.S. Pat. Nos. 6,896,758 and 5,271,786, incorporated here by reference. According to this manufacturing approach, a desired component is introduced to the central core of the extrusion die at the extruder head. In one arrangement, a first crimp is formed in the tubular wall as it exits the extrusion head, then a powder dose is advanced through an opening in the die core toward the first crimp, and then a second crimp is performed to seal a powder chamber. A similar method can be applied to the liquid filling. At least part of this process can be performed in a vertical direction to keep the dose adjacent to the first crimp.

In another preferred manufacturing method, at least one substance is lyophilized in the barrel, either prior or after creating the barrier between the first and the second substance compartments. In one arrangement, the device is intended for intramuscular vaccination. In one arrangement, the device is intended for intradermal vaccination in which case the fluid transport device may be a micro-needle or a needle with a limited skin penetration depth. Intradermal injection is typically set for smaller injectable volumes in the range of 0.1-0.15 ml and, therefore, the tubular wall diameter and the barrel's compartment lengths will be smaller than the dimensions proposed above for 0.5 ml dose.

In one arrangement, the device is intended for needle-free jet injection to the skin either for intradermal, subcutaneous or intramuscular administration, in which case the fluid transport device would be a jet-injector nozzle disposed at the contact surface of the device with the subject's skin. In one arrangement, the tubular section is substantially accommodated in a pressure chamber which serves as the actuator to which pressure is applied at the point of injection, and causes the tubular walls to collapse as the dispensable product is driven through the jet-nozzle. Alternatively, the dispensable product delivery can be driven by a piston or rollers.

The dispensing device of the present invention may be manually operated by a user in the same fashion that a regular syringe is. In one arrangement, the dispensing device is operated by an apparatus which manipulates the stem inwardly. In another arrangement, the device is operated by an apparatus where the apparatus provides the stem or other object for depleting the volume of at least one product or substance compartment. In one arrangement, the dispensing device is at least partially disposed in a pressure chamber of a dispensing apparatus such that when pressure is raised in the pressure chamber, the tubular wall collapses and dispenses the product. In one arrangement, the dispensing device serves as a cartridge for a dispensing apparatus. In one arrangement, the device is associated with at least one similar device to auto-load into a dispensing apparatus. In one arrangement, one device is linked with at least one similar device. In another arrangement, numerous devices are organized in a magazine.

In one arrangement, the tubular wall comprises at least one layer made from metal oxide, such as aluminum oxide or silicone oxide. The metal oxide layer may be applied by lamination, vapor deposition, or by one of the means known in the art.

The applications of the present invention are not limited to drug delivery which is provided here by way of example, and the teachings described herein can be applied to other applications of prefilled syringes such as glue dispensing, chemicals dispensing etc.

The present disclosure provides various configurations for accomplishing this.

BRIEF DESCRIPTION OF THE DRAWINGS

FIGS. 1A-1C illustrate a syringe barrel assembly that can be employed to various configurations;

FIG. 2 illustrates one arrangement of the syringe barrel comprising a needle assembly and plunger;

FIG. 3 illustrates an arrangement of the barrel where the needle assembly seals the dispensable product;

FIG. 4 illustrates an arrangement of the barrel where the plunger seals the dispensable product;

FIGS. 5A and 5B illustrate a reconstitution syringe assembly comprising two substance compartments;

FIGS. 12A-12F illustrate another preferred arrangement where the barrel is compressed by rollers and the reconstitution occurs when the stem is retracted;

DETAILED DESCRIPTION OF THE DRAWINGS

Figure 6A:
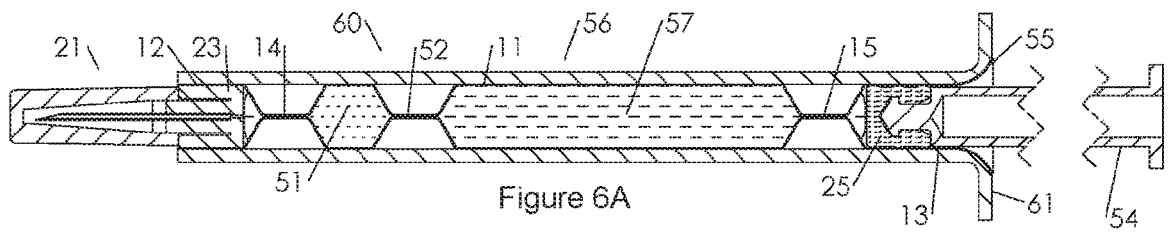
FIGS. 6A-6E illustrate the operation steps of one arrangement of a reconstitution syringe of the present disclosure.

FIG. 1A illustrates a barrel assembly 10 comprising a tubular wall section 11 having a distal end 12 and a proximal end 13. The tubular wall comprises a distal crimp 14 adjacent to the distal end 12, and a proximal crimp 15 adjacent to the proximal end 13 forming a confined volume in between.

FIG. 1B shows a top view of the barrel assembly 10 illustrating the section view line of FIG. 1C, along the axis of the tubular wall.

FIG. 1C illustrates a section view of the barrel assembly 10 according to the section line in FIG. 1B. The distal crimp 14 and the proximal crimp 15 form barriers along the tubular wall 11, defining a compartment therebetween, hermetically sealing a dispensable product dose 16. The barrel assembly, as illustrated in this arrangement, may provide a subassembly of a dispensing device such as a disposable syringe. The barrel assembly, as illustrated in this arrangement, may also serve as a cartridge for a nondisposable dispensing device. The tubular wall is made by co-extrusion of a multi-layer tube. One advantage of multi-layer extruded materials is that each layer can provide different properties that are important for the overall wall performance. One layer may provide a high barrier to oxygen or moisture which can be achieved with Aclar or COC. Another layer may provide the structural stability and strength of the tubular wall 11 and may be made from Polyethylene terephthalate (PET). The inner layer of the tubular wall may be an adhesive layer that will allow forming a seal at the pinched section. One advantage of coextruded tube wall is that a combination of important properties can be achieved at very low wall thickness which could not be achieved, for example, with a molded plastic wall with much greater wall thickness. The fluid tight barrier at the pinched section can be achieved by one of the means known in the art including heat stake sealing. Where the inner layer of the tubular wall 11 is an olefin ionomer blend such as the brand named product EasyPeel. A good seal can be achieved between 140° C. and 170° C.

In one arrangement, compartment 16 or a further compartment of the tubular section, is overwrapped with a high barrier foil wrap comprising a first side and a second side adhered to each other to define a sealed enclosure around said compartment. In at least one pinched section (14, 15 or other), each of the first side of the overwrap and the second side of the overwrap are adhered to a pinched section to complete an integral seal around said compartment. The overwrap can be removed to allow visual inspection of the tubular section or its content.

In one arrangement, compartment 16 or a further compartment of the tubular section, is overwrapped with an adhesive foil that is wound around the compartment to form a sealed enclosure around said compartment. The overwrap can be removed to allow visual inspection of the tubular section or its content.

FIG. 2 illustrates another preferred arrangement of the barrel assembly of the present invention in which a fluid transport device, in the form of an intramuscular (IM) hypodermic needle assembly 21, is disposed at its distal end 12 and a plunger 25 is disposed at its proximal end 13. The needle assembly 21 comprises a needle coaxially attached to a needle-hub 23, and a needle cap 24 engaged with said needle hub 23. The needle 22 may be attached to the needle hub by one of the means known in the art including adhesive, press-fit or heat seal. The needle may be made from stainless steel 316. The needle hub 23 may be made from a molded plastic material including Polyethylene (PE), Polypropylene (PP), COC, and COP. The needle-hub 23 comprises a cylindrical outer diameter which fits into the distal end 12 of the tubular wall 11 to form a fluid tight seal. The seal of the needle hub 23 to the tubular wall 11 may be achieved by one of the means known in the art including heat seal, adhesion, press-fit, external clamp that tightens the tubular wall 11 against the needle-hub 23, or a combination of the formers. The needle cap 24 press-fits with the needle-hub 23 and is removed at the time of use by a pull of or a twist-off action. In one arrangement, a tamper evident feature changes its form irreversibly when the needle-cap 24 is removed such that prior tampering of the dispensing device can be noticed. In one arrangement, the needle-cap aseptically seals to the needle-hub 24 to maintain the needle 22 sterility. In one arrangement, the needle-cap 24 provides a moisture and oxygen barrier to the dispensable product or substances in the barrel. The needle-cap may be made from molded plastic such as PP, PE, COC, COP, Polystyrene (PS), Polycarbonate (PC) or other materials known in the art. Other fluid transport devices, such as the examples listed earlier, may be incorporated with the barrel to serve for the particular use of the dispensing device. The plunger 25 is disposed in the proximal end 13 of the tubular wall 11 in a fluid tight fashion. The plunger can be made from semi-rigid molded plastic materials such as PE, or rubber materials such as Ethylene-Propylene-Diene (EPDM), Bromobutyl rubber (BIIR), Isoprene Rubber, or other materials known in the art.

FIG. 3 illustrates another preferred arrangement of the barrel assembly 30 mostly similar to the barrel arrangement 20 of FIG. 2 with the exception that the dispensable product 16 is confined in the tubular wall 11 between the proximal crimp 15 and the needle assembly 21. The needle cap 24 provides a moisture and oxygen barrier to the dispensable product 16.

FIG. 4 illustrates another preferred arrangement of the barrel assembly 40 mostly similar to the barrel arrangement 20 of FIG. 2 with the exception that the dispensable product 16 is confined in the tubular wall 11 between the distal crimp 14 and the plunger 25. The plunger 25 provides a moisture and oxygen barrier to the dispensable product 16.

FIGS. 5A and 5B illustrate a preferred arrangement 50 of the dispensing device of the present invention. The tubular wall section 11 of the barrel assembly 56 comprises a distal crimp 14, a proximal crimp 15, and an intermediate crimp 52 defining a proximal compartment 57 holding a first substance and a distal compartment 51 holding a second substance. A stem 54 is associated with the plunger 25 at the proximal end of the barrel 56 for operating the plunger 25 as will be illustrated in the following figures. The proximal end of the tubular wall 13 is expanded to form a flare 55. The flare 55 can be produced by one of the means known in the art including compression with a hot die. A finger flange 53 comprises a tubular distal end that mounts over the tubular wall 11; two lateral protrusions extending from its proximal end; and an intermediate section with a profile that follows the flare 55 for attaching the finger flange 53 to the flare 55. The finger flange 53 and the tubular wall can be attached by one of the means known in the art including adhesives, heat welding, etc. One way to operate the dispensing device 50 is for the user to place her/his index and middle fingers on the finger flange and press the stem toward the barrel with the thumb. Another way to operate the dispensing device 50 is for the user to hold the finger flange between the thumb and middle finger and press the stem toward the barrel with the index finger. The stem can be operated by a dispensing apparatus.

Referring now to FIG. 6A, a further preferred arrangement 60 is illustrated, mostly similar to arrangement 50 of FIGS. 5A and 5B with the exception that the finger flange extends in the form of a sheath 61 coaxially with the barrel assembly 56 from its proximal end 13 to its distal end 12. The sheath provides a structural element to the dispensing device 60. It is attached to the proximal end of the tubular wall in the same fashion as the finger flange 53 of FIGS. 5A and 5B does. At the distal end, the sheath 61 is attached to the barrel 56 by press fit on the tubular wall 11 and the needle hub 23. This press fit may also contribute to the seal between the tubular 11 and the needle-hub 23.

Figure 6B:
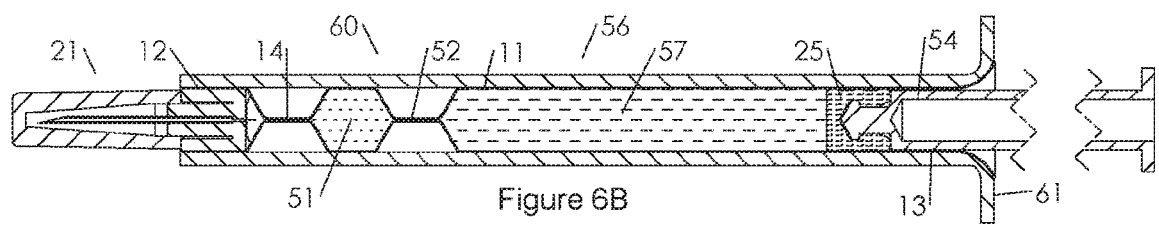

FIG. 6B illustrates the dispensing device 60 where the plunger 25 is advanced with the stem 54 an incremental distance toward the distal end by the stem. The plunger 25 pushed through the proximal pinched section 15, causing the seal to rupture and for the pinched section to restore its tubular shape.

Figure 6C:
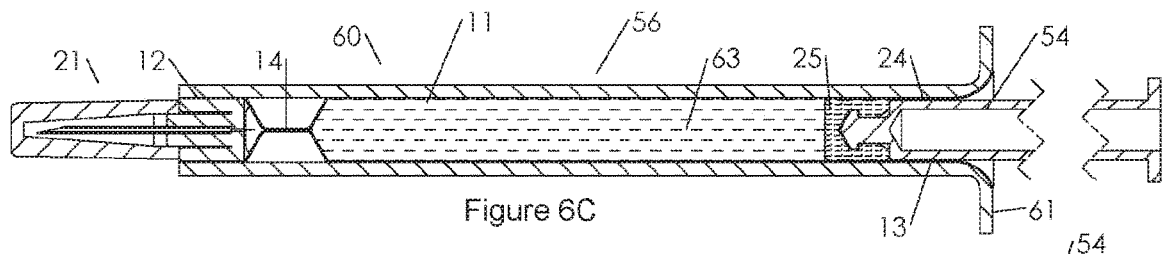

FIG. 6C illustrates the dispensing device 60 where the plunger 25 is further advanced with the stem 54 another incremental step toward the distal end of the barrel. As the plunger 25 moves toward the distal end, the pressure of the first substance 57 increases causing the seal at the intermediate pinched section 52 to rupture and for the intermediate pinched section 52 to restore its tubular shape. The first substance and the second substance are allowed to mix to form the dispensable product 63.

Figure 6D:
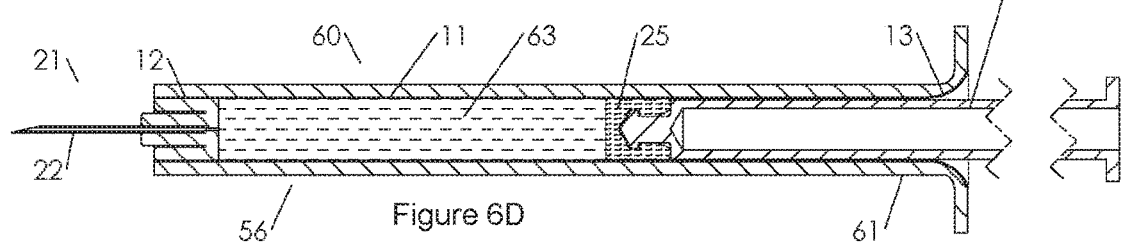

FIG. 6D illustrates the dispensing device 60 where the plunger 25 is further advanced with the stem another incremental step toward the distal end of the barrel. As the plunger 25 advances, the pressure of the product 63 increases causing the seal at the distal pinched section 14 to separate and for the distal crimp 14 to restore its tubular shape. A flow communication is established between the product 63 and the needle 22.

Figure 6E:
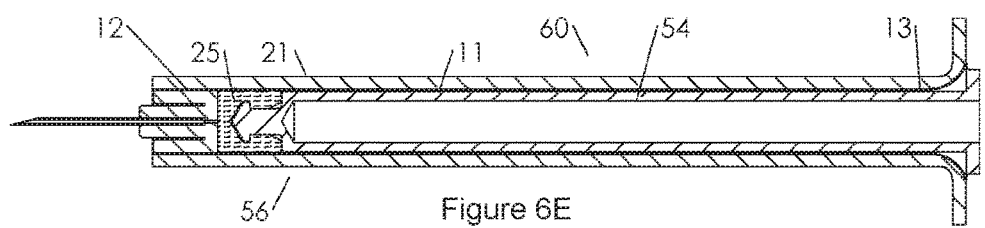

FIG. 6E illustrates the dispensing device 60 where the plunger 25 is advanced by the stem to the distal end of the barrel causing the product to dispense.

Figure 7A:
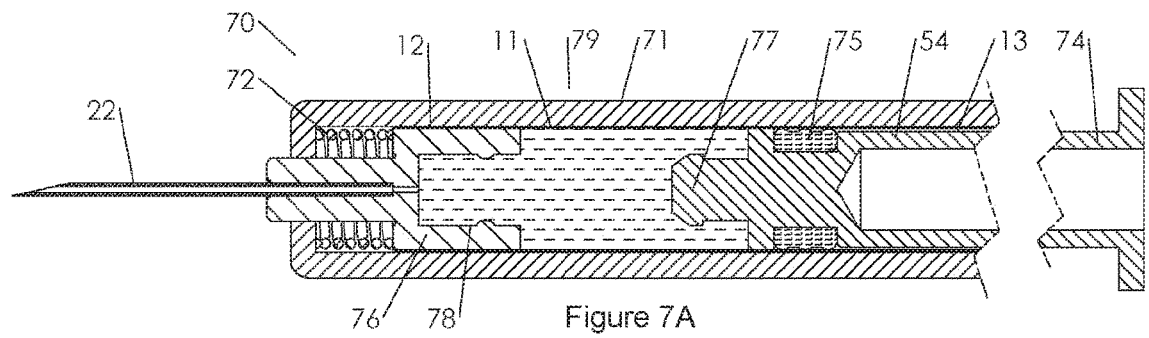
FIGS. 7A-7C illustrate a further preferred arrangement including a needle stick safety mechanism.

FIG. 7A illustrates another preferred arrangement 70 which comprises a needle-stick safety mechanism. The stem 74 comprises a seal gland at its distal end in which an annular seal 75 is disposed providing a fluid tight seal to the proximal end of the tubular wall 11. The stem 74 further comprises at its distal end a detent feature 77. The barrel assembly 79 is movably disposed in a sheath 71. A spring 72 is disposed between the distal end of the barrel assembly 79 and an inward protruding wall of the sheath 71 biasing the barrel assembly 79 toward the proximal side of the sheath 71. A detent mechanism (not shown) prevents the barrel assembly 79 from moving toward the proximal end of the sheath 71.

Figure 7B:
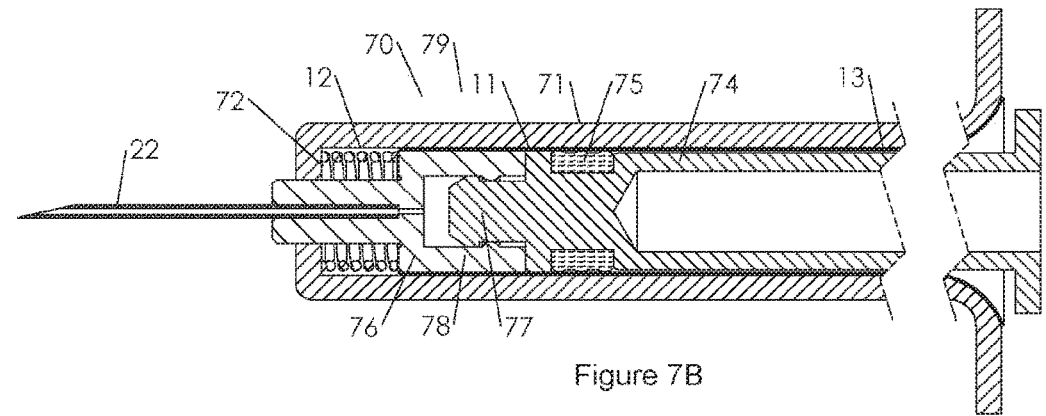

Referring now to FIG. 7B, the device 70 is shown when the stem 74 is advanced to the distal end of the barrel assembly 79, dispensing the product 16. The detent feature 77 is engaged now with the circular protrusion 78 of the needle-hub 76. The stem 74 slightly pushes the barrel assembly against the spring 72 thereby releasing the barrel assembly 79 from the sheath 71.

Figure 7C:
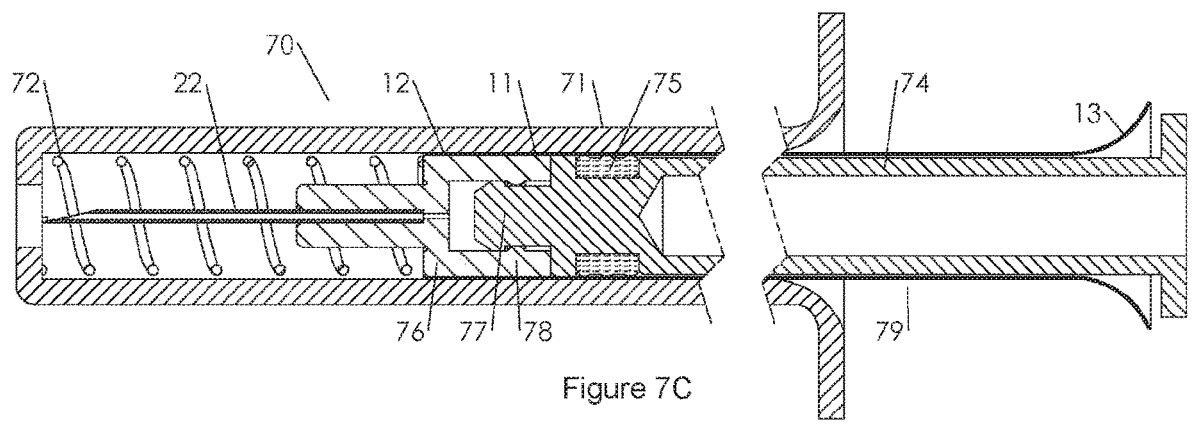

Referring now to FIG. 7C, when the inward force on the stem 74 is released, the spring retracts the barrel assembly and the needle 22 disappears into the sheath 71, thereby preventing possible injury from the needle tip. The barrel assembly 79 may also be retracted by pulling the stem 74 back without the need of the spring.

Figure 8A:
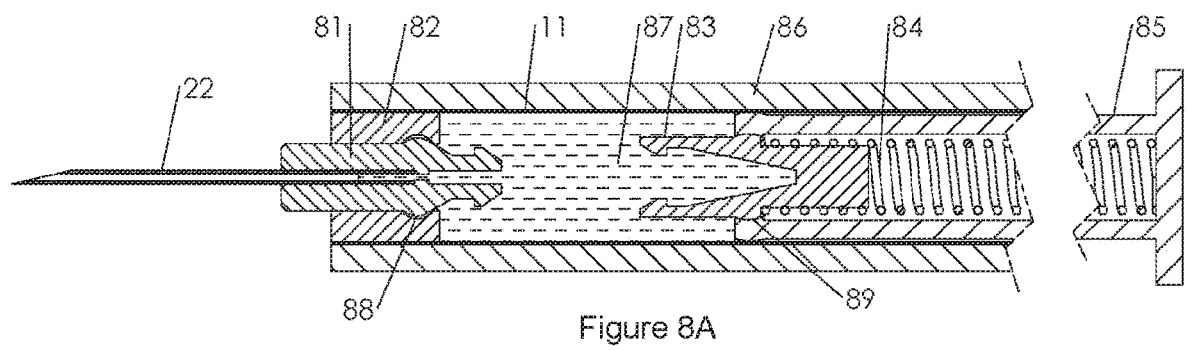
FIGS. 8A-8C illustrate a further preferred arrangement employing another needle stick safety mechanism and disabling mechanism to prevent a subsequent use of the syringe.

FIG. 8A illustrates another preferred arrangement 80 comprising an auto-disable mechanism that prevents a subsequent use of the dispensing device 80. A spring 84 is disposed in the stem 85 and is biasing gripper part 83 into the stem. The gripper 83 is engaged in a recess on the interior wall of the stem 85, preventing the gripper 83 from retracting into the stem 85. The stem further comprises a lateral protrusion that seals against the tubular wall 11 thereby creating a fluid tight seal without a dedicated resilient seal part. At the distal end of the barrel, a coupling unit 82 is sealed against the tubular wall 11. The needle-hub 81 is mechanically engaged, in a fluid tight seal fashion, with the coupling unit 82 via a circular groove 88 in the coupling unit which receives a protrusion from the needle hub 81.

Figure 8B:
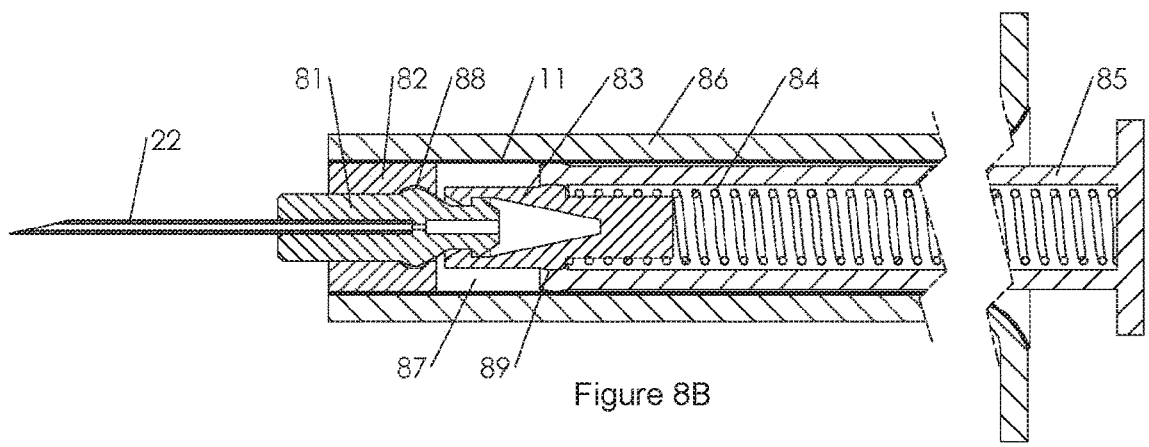

Referring to FIG. 8B, the device 80 is shown where the stem is progressed toward the proximal end of the barrel and the product 87 is dispensed. The gripper part 83 is now engaged with a reciprocal feature of the needle hub.

Figure 8C:
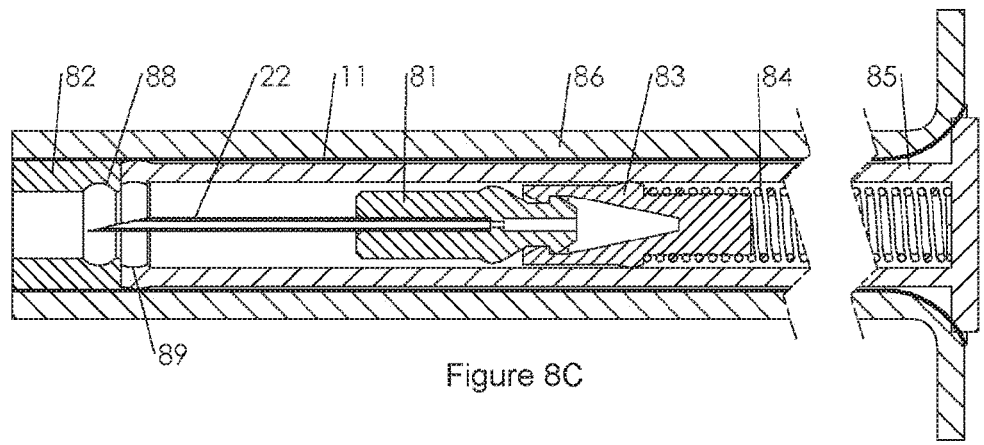

Referring to FIG. 8C, the stem is further pushed into the barrel causing the needle-hub 81 to disengage from the coupling unit 82 and for the gripper part 83 to disengage from the detent groove 89 in the stem 85, thereby allowing the spring to retract the gripper 83 with the needle 22 and the needle-hub 81 into the stem 85. In this position, the device cannot be used again.

Figure 9A:
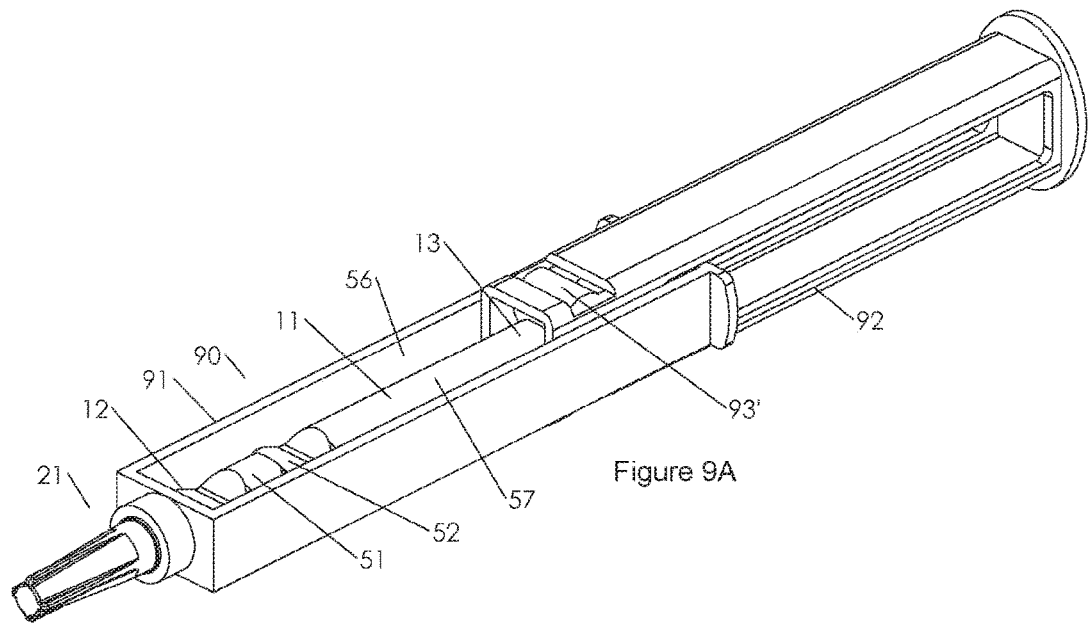
FIGS. 9A-9C illustrate a further preferred arrangement where the barrel is compressed by rollers to deliver the dispensable product.

Referring now to FIG. 9A, a further arrangement 90 of the dispensing device is illustrated. The dispensing device 90 comprises a barrel assembly 56 enclosed in a frame 91, said frame 91 providing a guidance for a stem 92 to move along the frame 91 and the barrel assembly 56 in an axial direction. Two rollers are accommodated in the distal end of the stem 92-93' and the other is not shown.

Figure 9B:
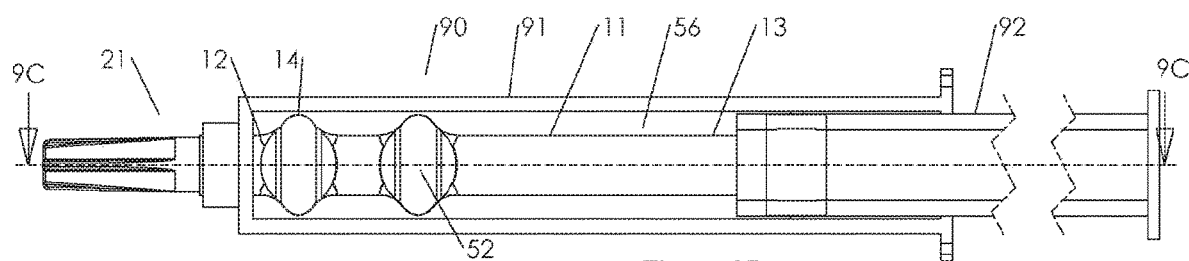
Figure 9C:
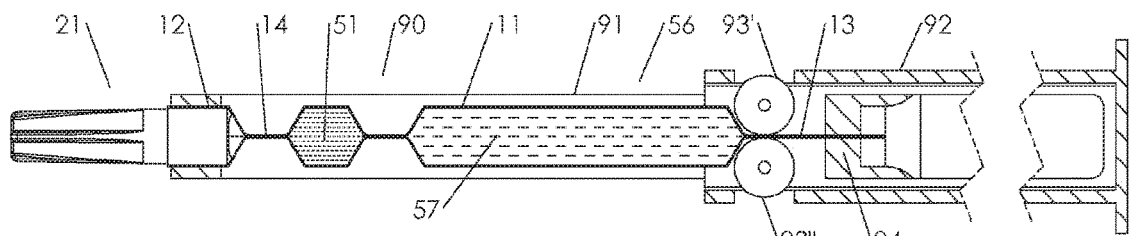

FIG. 9B illustrates the section line for FIG. 9C along the axis of the barrel assembly. FIG. 9C illustrates a section view of the dispensing device 90 along the section line provided in FIG. 9B. The shafts of rollers 93' and 93" communicate with the stem 92 such they move together along the barrel 56 axis. As the stem 92 is advanced, the tubular wall 11 is compressed between the two rollers 93' and 93" causing a similar sequence of events as illustrated in FIGS. 6A-6E when the plunger progresses in the barrel. One advantage of this arrangement is that the proximal end of the barrel assembly remains sealed reducing risk of contamination. Another advantage of this arrangement is that it avoids the friction of a rubber plunger in the barrel.

Figure 10A:
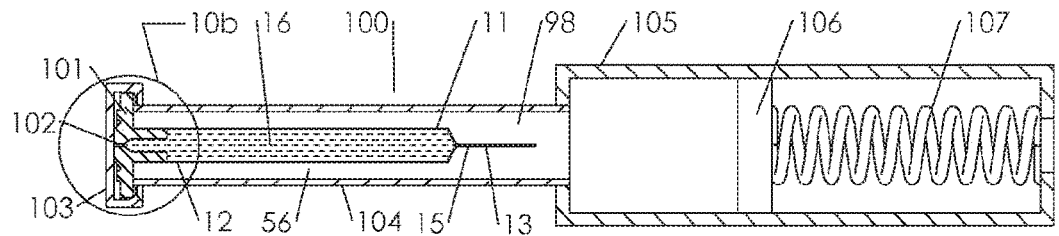
FIGS. 10A-10D illustrate a preferred arrangement where the device is a needle-free jet injector operated by pressure provided by a spring force.

FIG. 10A illustrates a jet injector configuration. For jet injection, substantial pressure needs to be developed in a very short time. The device 100 comprises a barrel assembly 56, enclosed in a pressure chamber 108. At the distal end of the pressure chamber 108, a piston 106 is biased by a spring toward the distal end of the chamber 108, and is detent by a detent mechanism (not shown) at this position until the injection time.

Figure 10B:
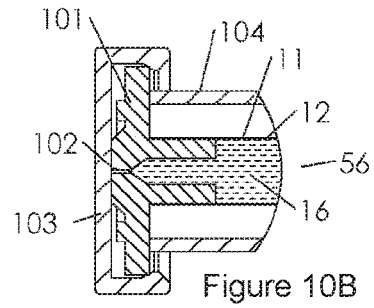

FIG. 10B illustrates a detail view of the fluid transport device 101 comprising a jet nozzle 102 at its center. The proximal end of the fluid transport device 101 is sealed against the tubular wall 11. In the center of the fluid transport device 101, a small bore provides the jet nozzle 102. The nozzle 102 is covered by a cover 103 until the time of use.

Figure 10C:
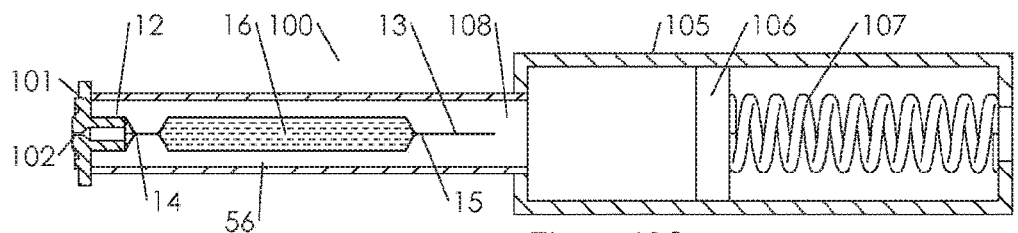

FIG. 10C shows one configuration of the jet injector 100 where a crimp 14 in the tubular wall 11 separates the injectable product 16 from the nozzle. Prior to use the barrel is accessed to depress the tubular wall to pressurize the product 16 which will cause the barrier at the pinched section 14 to rupture and for a fluid communication to be established between the product 16 and the nozzle 102.

Figure 10D:
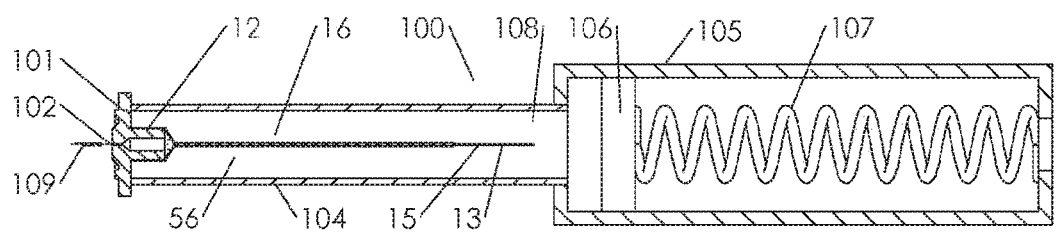

FIG. 10D illustrates the device 100 after the cover 103 has been removed, and the piston 106 has been released allowing the spring 107 to displace the piston toward the barrel 56 causing an instant pressure rise in the pressure chamber 108. In return, the pressure in the chamber 108 causes the tubular wall to collapse delivering a pressurized product 16 through the nozzle 102 in a thin jet format 109.

Figure 11:
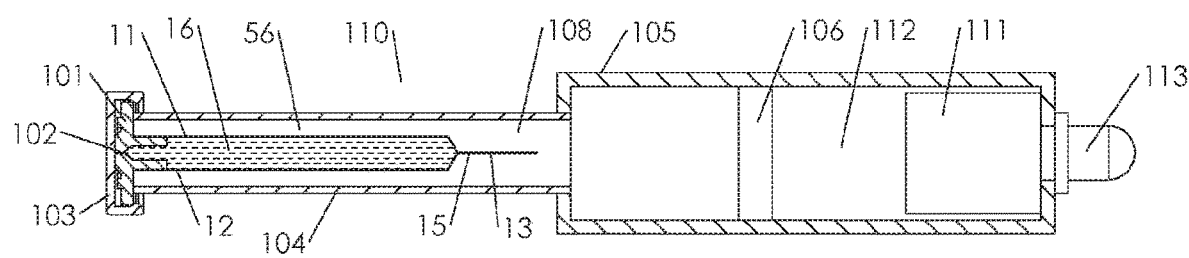
FIG. 11 illustrates a preferred arrangement where the device is a needle-free jet injector operated by pressure provided by a chemical reaction.

FIG. 11 shows a further preferred arrangement of a jet injector substantially similar to arrangement 100 of FIGS. 10A-10D with the exception that the piston is forced forward by a pressure generated in a second pressure chamber 112. A pyrotechnic module 111 is activated by pressing the button 113 at its rear end to create a small explosion which instantly builds pressure and advances the piston 106 forward to cause the jet injection as described in FIGS. 10A-10D. In one arrangement, the piston is eliminated and the pressure created by the module 111 directly applies to the tubular wall.

FIG. 12A illustrates a preferred arrangement of the present invention in which, as in FIGS. 9A and 9B, the tubular wall is collapsed via a couple of rollers associated with the stem. The figure shows the assembled device 120 at the pre-use position where the stem 121 is advanced to the distal end of the barrel assembly 56. A frame 122 is disposed along the barrel and guides the stem 121.

FIG. 12B illustrates an exploded view of device 120 at the same pre-use position as in FIG. 12A. The two compression rollers 93' and 93" are inserted through bores at the side walls of the stem 121, at the end of upper and lower cantilever arms. The shafts 123' and 123" of the rollers 93' and 93" extend through the walls of the stem 121. The shafts 123' and 123" engage in the guiding ribs 124 in the side walls of the frame 122, such that when the stem is manipulated along the axis of the barrel 56 and the frame 122, the rollers will move toward or away from each other in a radial direction as they move along the axis of the barrel. The cantilever arms of the stem 121 will flexure as the rollers move in a radial direction. The barrel assembly 56 is disposed in the frame 122 which firmly holds the proximal end 12 and the distal end 13 of the barrel 56. The barrel is separated into two substance compartments—a proximal compartment between the proximal pinched section 15 and the intermediate pinched section 52, and a distal compartment between the distal pinched section 14 and the intermediate pinched section 52.

Figure 12C:
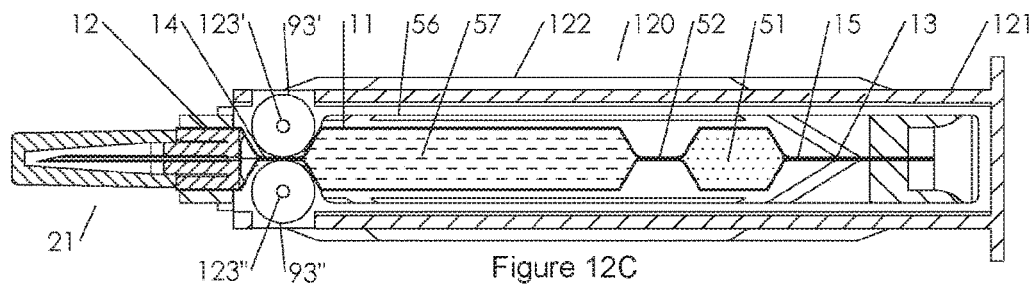

FIG. 12C illustrates a section view of the dispensing device 120 prior to use. At this position, the stem is advanced toward the distal end 13 of the barrel assembly 56. Rollers 93' and 93" are located at the area of the distal pinched section 14. The barrel 56 comprises a distal substance compartment with a fluid substance 57 and a proximal compartment with a second substance 51; the two substances need to be mixed to form the dispensable mixture or product. One advantage of this arrangement 120 is its compact size at the pre-use packaged configuration since the stem 121 is advanced such that it does not contribute significantly to the packaged volume.

Figure 12D:
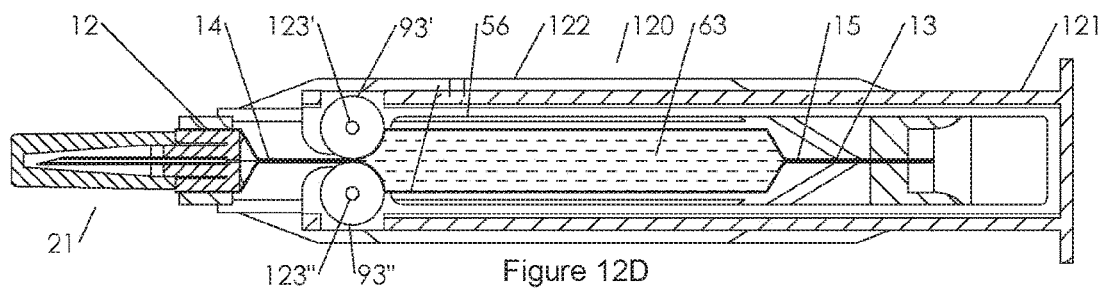

FIG. 12D demonstrates the device 120 after the stem 120 has been incrementally pulled out such that the rollers slightly compress the distal compartment causing the fluid substance 157 to pressurize and rupture the seal at the intermediate crimp section 52, allowing it to mix with the second product 51 to form the dispensable product 63. The fluidic substance 57 may be in any of the forms known in the art including liquid, gel, paste, slurry, gas, suspension, mixture, solution, flowable powder or a combination of the above. The second substance 51 may be in any of the forms known in the art including liquid, gel, paste, slurry, gas, suspension, mixture, solution, flowable powder, solid, compressed powder granules, cake, lyophilized cake, or a combination of the above. The dispensable product 63 may be a product of a chemical reaction of the first and the second substances 51 and 57, a mixture, a solution, a suspension, liquid, gel, paste, slurry, gas, flowable powder or a combination of the above.

Figure 12E:
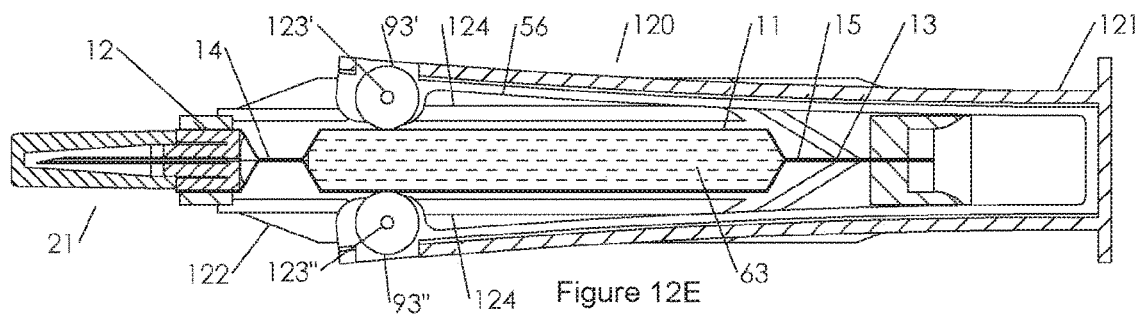

FIG. 12E shows the device 120 after the stem 121 has been retracted by another incremental distance. The guides (not shown) on the frame 122 divert the roller shafts 123' and 123" away from each other in a lateral direction as the rollers 93' and 93" move with the stem 121 in an axial direction, causing the rollers 93' and 93" and the cantilever arms of the stem 121 to move apart. In this position, the rollers no longer compress the tubular wall 11.

Figure 12F:
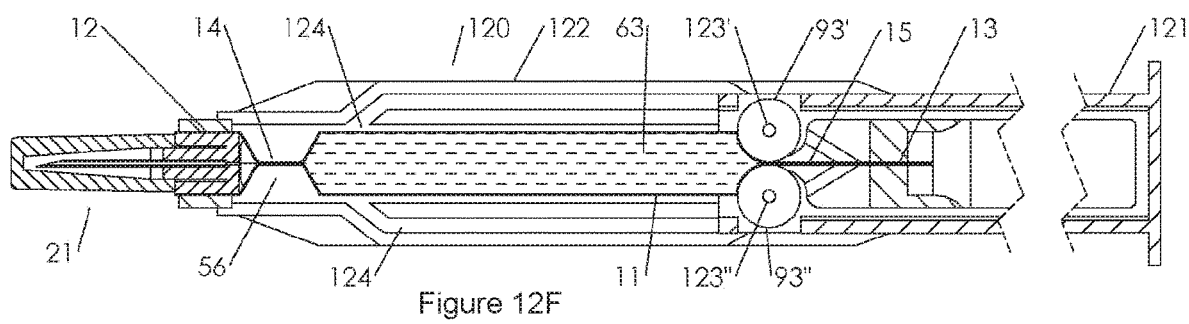

Referring now to FIG. 12F, the device 120 is now shown in the ready-for-injection position, after the stem 121 has been retracted completely such that the rollers 93' and 93" are now positioned behind the product compartment ready to squeeze the tubular wall 11 toward the fluid transport device 21 and express the product 63 in that process. The rollers were retracted to this position while they were spaced apart, and the guides on the frame's 122 walls allowed them to return to the closer position at this position. As the stem will be pushed in for injection, the guides will maintain the rollers 93' and 93" pressed toward one another to allow for efficient expression of the product 63. It will be obvious to those skilled in the art that a needle-stick safety feature as well as an auto-disabling feature may be combined in the device 120. A tamper evident feature may be combined in the device 120.

Figure 13:
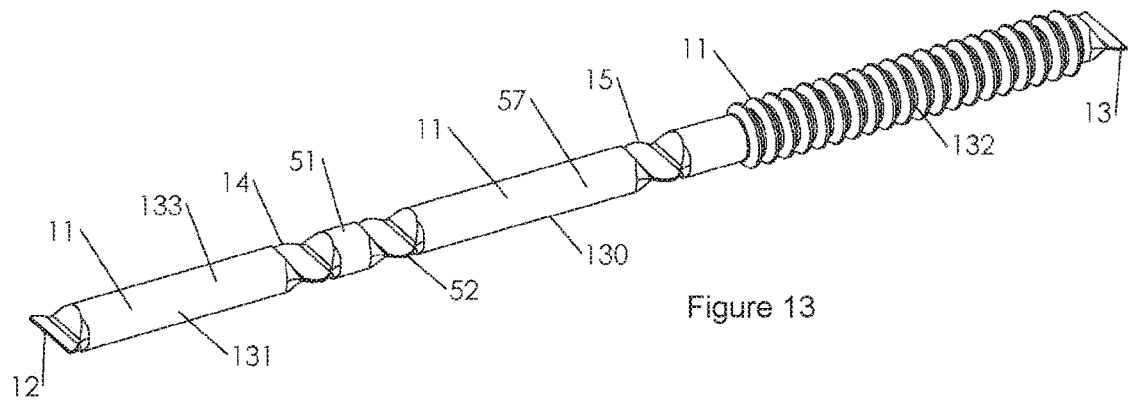
FIG. 13 illustrates another arrangement where the tubular wall extends to provide an aseptic cover to the distal end and the proximal end of the injection device.

Referring to FIG. 13, the tubular wall 11 is extended at its distal end 12 forming a distal extended portion 131 which covers over the needle assembly (not shown—21 in earlier Figures). Proximal end 12 of the extended portion 131 is pinched and sealed to form an aseptic enclosure to the needle assembly and ensure its sterility. The extended section 131 may also provide mechanical protection to a needle and may eliminate the need for a needle shield as shown in earlier Figures. The distal extending portion 131 may be removed to expose the fluid transport device. In one arrangement, the distal extended portion 131 is removed by twisting it off. A weakened section about where number 133 points defines the breaking off zone of the distal extended portion 131. The tubular wall also extends at its proximal end forming a proximal extended portion 132 pinched and sealed at its proximal end 13, providing an aseptic enclosure to the piston shown in earlier figures. The proximal extended section is corrugated in a form of a bellows axially movable between a pre-injection position to an injection position, allowing manipulation of the piston to operate the delivery device 130.

Figure 14:
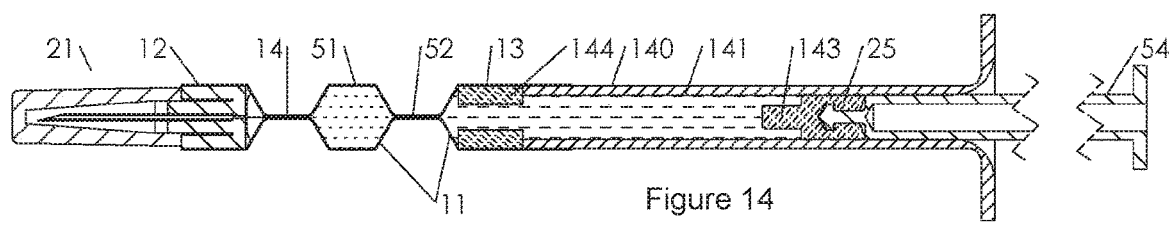
FIG. 14 illustrates another arrangement where the tubular wall is attached to the outer diameter of a rigid syringe barrel and where the syringe's plunger advances into the powder compartment during injection.

Referring now to FIG. 14, the tubular wall 11 forms a substance compartment 51 defined by the pinched and sealed sections 14 and 52. The proximal end 13 of the tubular wall 11 is attached to the outer diameter of a rigid barrel 141 of a syringe, prefilled with a flowable substance 145. An annular second plunger 144 is coaxially disposed between the proximal barrier 52 and the rigid barrel 141, axially movable toward the distal end 12 of the tubular wall 11. A first plunger 25 is disposed at the proximal end of the rigid barrel 141, and is movable with stem 54 along the axis of the barrel 141. The arrangement is such that when the first plunger 25 is advanced toward the distal end of the device 140, it causes the first substance 145 to pressurize and rupture the proximal barrier 52, allowing the first substance 145 and the second substance 51 to mix and form the dispensable product. Further advancement of the plunger 25 toward the distal end of the device 140 will cause the product to pressurize and rupture the distal barrier 14, thus establishing communication between the product and the fluid transport device 21. As the plunger is furthered advanced in the rigid barrel 141, the product is expressed from the device 140 through the fluid transport device 21. As the first plunger 25 reaches the distal end of the rigid barrel 141, it engages in a sealed fashion with the second plunger 144, and from this point, the two plungers advance together when the stem 54 is further manipulated into the rigid barrel 141 to express the remaining dose from tubular wall section 11. The second plunger 144 has a larger diameter than the first plunger 25 providing a fluid tight seal against the tubular wall 11. An axial protrusion 143 of the first plunger 25, fits the annular bore of the second plunger 144 when the two engage to eliminate residues of the product in that area. U.S. Pat. No. 7,850,663 to Sullivan teaches a method and device for intradermal delivery of a reconstituted powdered medicament. The device includes a chamber, which is in fluid communication with a microdevice, e.g. microabrader or one or more microneedles. A cartridge containing the powdered medicament may be located within said chamber. At least one burstable membrane retains a powdered medicament within the housing. The method involves the steps of positioning the device at a delivery site on the skin of a patient and intradermally administering the medicament by dispensing a diluent from a diluent source, through an inlet port to rupture the membranes, reconstitute the powdered medicament and deliver the reconstituted medicament through the microdevice to the dermal region of the skin. Unlike the arrangement 140 of FIG. 14, and as illustrated in Sullivan's FIG. 5D, a substantial residue of the delivered product remains at the end of the injection in the powder compartment, sometimes referred to as "dead space". This is addressed in FIG. 14 of the present disclosure by providing a protrusion 143 to the first plunger that evacuates the dispensable product from the bore of the second plunger 144. US Pat. Application 20060276755 to Sullivan teaches a valved medicament delivery device including a housing having a chamber, including a coaxially aligned inlet and outlet, a medicament cartridge located within the chamber having a passage there through and membranes sealing the passage having a burst pressure of less than 10 atmospheres, a manually actuatable fluid delivery device having an outlet in fluid communication with the chamber and a manually actuated valve located between the outlet of the fluid delivery device and the chamber inlet for delivery of fluid under pressure to the valve. The medicament delivery device of this invention may be utilized to deliver a controlled unit dose of a medicament on demand by first pressurizing a pressure chamber in the pressure delivery device upstream of the valve, then opening the valve to open the membranes and express the medicament through the chamber outlet. FIGS. 3 and 4 in Sullivan's application illustrate a foil forming a barrier between a powder substance and water. This arrangement may result in substantial moisture transfer through the foil and damage the powder substance. This disadvantage is addressed in FIG. 14 of the present disclosure as well as in other arrangements of this disclosure as the tubular wall does not constitute a barrier between two substances. Instead, a substantially wide sealed section 52 constitutes the barrier between the first and the second substance and eliminating the risk of moisture transfer to a dry substance. The rigid barrel 141 may be made from Polypropylene and the tubular section 11 may be attached to it through thermal welding or through any other method known in the art. In one arrangement, the rigid barrel 141 is attached to the tubular wall 11 by over-molding (insert-molding) the rigid barrel 141 onto the tubular wall 11.

Figure 15:
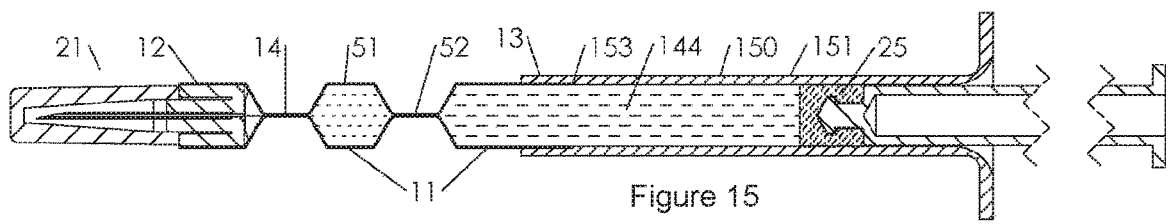
FIG. 15 illustrates another arrangement where the tubular wall is attached to the inner diameter of a rigid syringe barrel, and where the syringe's plunger advances into the powder compartment during injection.

Referring to FIG. 15, the tubular wall 11 forms a substance compartment 51 defined by the pinched and sealed sections 14 and 52. The proximal end 13 of the tubular wall 11 is attached to a recessed section 153 of the inner diameter of a rigid barrel 151 of a syringe, prefilled with a flowable substance 155. A plunger 25 is disposed at the proximal end of the rigid barrel 151, and is movable by manipulation of stem 54 along the axis of the barrel 141. The arrangement is such that when the plunger 25 is advanced toward the distal end of the device 150, it causes the first substance 155 to pressurize and rupture the proximal barrier 52, allowing the first substance 155 and the second substance 51 to mix and form the dispensable product. Further advancement of the plunger 25 toward the distal end of the device 150 will cause the product to pressurize and rupture the distal barrier 14, thus establishing communication between the product and the fluid transport device 21. As the plunger 25 is furthered advanced in the rigid barrel 141, the product is expressed from the device 140 through the fluid transport device 21. The rigid barrel 151 may be made from Polypropylene and the tubular section 11 may be attached to it through thermal welding or through any other method known in the art. In one arrangement, the rigid barrel 151 is attached to the tubular wall 11 by over-molding (insert-molding) the rigid barrel 151 onto the tubular wall 11. The recessed section 153 of the rigid barrel 151 where the tubular wall 11 is attached allows maintaining a uniform inner diameter between the rigid barrel 151 and the tubular wall 11 ensuring reliable fluid tight seal with the plunger 25 along its entire travel.

Figure 16:
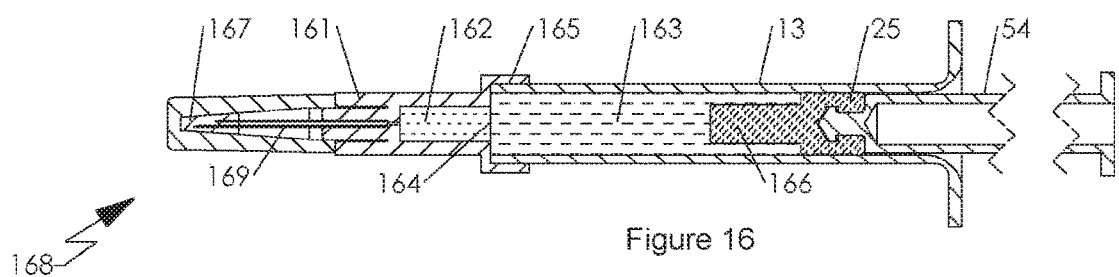
FIG. 16 illustrates another arrangement of a syringe where the plunger advances into the powder compartment during injection.

FIG. 16 illustrates a syringe arrangement comprising: a syringe barrel 13 defining a first constituent compartment 153 between a plunger 25 at the proximal end of the barrel 13 and a rupturable membrane 164 at the distal end of barrel 13. A needle assembly 168 comprises a needle hub 161, attached to a needle 169. The needle hub 161 further defines a compartment for a second constituent 162, and sealed by membrane 164. The second compartment 162 is in fluid communication with the proximal end of the needle and the distal end of the needle 169 is sealed with a needle stopper 167 to contain the second constituent 162 aseptically sealed. The proximal end of the needle hub 165 is attached to the barrel 13 in a fluid tight fashion by one of the attachment methods known in the art including heat stake welding, spin welding, ultrasonic welding, RF welding, via adhesives, a press fit, and a tight thread. In one arrangement, the membrane 164 is attached to the needle assembly 168, maintaining the second constituent aseptically sealed, prior to integration with the syringe barrel 13. In one arrangement, the membrane 164 is attached to the barrel 13, maintaining the first constituent aseptically sealed, prior to integration with the needle assembly 168. In one arrangement, membrane 164 consists of a first layer, attached to the needle hub 161, and a second layer attached to the syringe's barrel 13 prior to the assembly of the needle assembly 168 and the barrel 13. In this arrangement, the first membrane layer maintains the second constituent aseptically sealed prior to assembly with the barrel, and the second layer maintains the first constituent aseptically sealed prior to integration with the needle assembly 168. In this case, the integration of the syringe barrel 13 and the needle assembly 168 may be performed in the manufacturing process or in the field just prior to injection or elsewhere. A protective cap may be disposed to protect the membrane or the membrane layers discussed above. For injection, the syringe's plunger 25 and piston 54 are advanced to pressurize the first constituent 153 and rupture membrane 164, and allow the first and second constituents to merge. Further advancement of the plunger 25, with the needle cap removed, will express the merged first and second constituents 153, 164 through the needle. At the end of the injection process, protrusion 166 of the plunger 25 at least partially penetrates the second compartment 162 to reduce the product residues in the syringe. A rupturing member may be associated with the membrane 164 to facilitate the membrane rupturing when the first constituent 153 is pressurized. In the arrangement discussed above where the membrane 164 consists of multiple layers, the rupturing member may be accommodated between these layers, Accordingly, the present invention has been described with some degree of particularity directed to the exemplary arrangements thereof. It should be appreciated, though, that the present invention is defined by the following claims construed in light of the prior art so that modifications or changes may be made to the exemplary arrangements of the present invention without departing from the inventive concepts contained herein.

What is claimed is:

1. A dispensing device for use with a beneficial agent, comprising:
    a dispensing package, comprising:
        an elongate, at least partially flexible member comprising a sealed, pre-formed tubular compartment and at least one separable barrier enclosing one end of said tubular compartment, wherein said tubular compartment includes at least a first compartment; and
        one of the beneficial agent or a constituent of the beneficial agent contained in said tubular compartment;
    a dispenser disposed on a dispensing end portion of said dispensing package; and
    a rigid sealed pressure chamber enclosing at least a portion of said tubular compartment and configured such that elevated pressure in a space defined between said rigid sealed pressure chamber and said at least partially flexible member comprising said tubular compartment results in expulsion of said beneficial agent or said constituent of the beneficial agent from at least said tubular compartment.

2. The dispensing device according to claim 1 wherein said at least one separable barrier is formed along a tubular wall of said tubular compartment by pinching said one end of said tubular compartment and thereafter sealing across said one end.

3. The dispensing device according to claim 1 wherein said at least one separable barrier defines a distal end of said tubular compartment.

4. The dispensing device according to claim 2 wherein said tubular wall of said tubular compartment comprises a multi-layer material.

5. The dispensing device according to claim 2 wherein said tubular wall of said tubular compartment is made by an extrusion process.

6. The dispensing device according to claim 5 wherein said tubular wall of said tubular compartment is made from an extruded sheet rolled and seamed to form a tube.

7. The dispensing device according to claim 1 wherein said separable barrier defines a proximal end of said first compartment.

8. The dispensing device according to claim 1 wherein said first compartment stores a first constituent of the beneficial agent, and the tubular compartment further comprising at least a second compartment storing a second constituent of the beneficial agent, and wherein said at least one separable barrier is located between said first and second compartments.

9. The dispensing device according to claim 1 wherein said at least one separable barrier is located between said first compartment and said dispensing end portion.

\* \* \* \* \*